(12) United States Patent
Tzeng et al.

(10) Patent No.: US 6,716,236 B1
(45) Date of Patent: Apr. 6, 2004

(54) INTRAVASCULAR CATHETER WITH HEAT EXCHANGE ELEMENT HAVING INNER INFLATION ELEMENT AND METHODS OF USE

(75) Inventors: Elbert Tzeng, Irvine, CA (US); Peter Barker, Oceanside, CA (US); Scott M. Evans, Santa Ana, CA (US); Wayne A. Noda, Mission Viejo, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 10/045,936

(22) Filed: Oct. 19, 2001

Related U.S. Application Data

(63) Continuation-in-part of application No. 09/503,014, filed on Feb. 11, 2000, now Pat. No. 6,409,747, which is a continuation of application No. 09/063,984, filed on Apr. 21, 1998, now Pat. No. 6,126,684.

(51) Int. Cl.$^7$ .................................................. A61F 7/00
(52) U.S. Cl. ........................ 607/105; 607/106; 607/113
(58) Field of Search .......................... 607/96, 104, 105, 607/106, 113

(56) References Cited

U.S. PATENT DOCUMENTS

| 2,058,780 A | 10/1936 | Elliott |
| 2,077,453 A | 4/1937 | Albright |
| 2,190,384 A | 2/1940 | Newman |
| 2,308,484 A | 1/1943 | Auzin et al. |
| 3,125,096 A | 3/1964 | Antiles et al. |
| 3,140,716 A | 7/1964 | Harrison et al. |
| 3,142,157 A | 7/1964 | Podolsky |
| 3,238,944 A | 3/1966 | Hirschhorn |
| 3,282,267 A | 11/1966 | Eidus |
| 3,327,713 A | 6/1967 | Eidus |
| 3,425,419 A | 2/1969 | Dato |
| 3,460,538 A | 8/1969 | Armstrong |
| 3,504,674 A | 4/1970 | Swenson et al. |
| 3,738,372 A | 6/1973 | Shioshvili |
| 3,776,241 A | 12/1973 | Magilton et al. |

(List continued on next page.)

FOREIGN PATENT DOCUMENTS

| WO | WO 91/05528 | 5/1991 |
| WO | WO 98/26831 | 6/1998 |
| WO | WO 98/31312 | 7/1998 |

OTHER PUBLICATIONS

U.S. patent application Ser. No. 09/266,452, Evans et al., pending.
U.S. patent application Ser. No. 09/294,080, Walker et al., pending.

(List continued on next page.)

Primary Examiner—Roy D. Gibson
(74) Attorney, Agent, or Firm—John L. Rogitz

(57) ABSTRACT

An intravenous catheter system (apparatus and method) for controlling patient temperature includes a generally tubular elongate body, a heat exchange element through which a heat exchange fluid circulates, and an inflation element or irregular surface positioned within the heat exchange element for promoting mixing of the circulating heat exchange fluid. The heat exchange element and inflation element preferably include inflatable balloons. The catheter preferably has two to four balloons having a substantially straight configuration, each balloon containing an inner balloon inflation element having a substantially spiral configuration. The catheter also preferably has at least one infusion lumen for providing access to the patient's blood and a guidewire lumen to accommodate a guidewire. The catheter is used in conjunction with a heat/cool system to cool a hyperthermic patient as quickly as possible, to warm a hypothermic patient as quickly as possible or to maintain normothermia.

16 Claims, 5 Drawing Sheets

U.S. PATENT DOCUMENTS

| | | |
|---|---|---|
| 3,897,790 A | 8/1975 | Magilton et al. |
| 3,913,581 A | 10/1975 | Ritson et al. |
| 4,010,795 A | 3/1977 | Stenberg |
| 4,111,209 A | 9/1978 | Wolvek et al. |
| 4,154,245 A | 5/1979 | Daily |
| 4,160,455 A | 7/1979 | Law |
| 4,181,132 A | 1/1980 | Parks |
| 4,249,923 A | 2/1981 | Walda |
| 4,298,006 A | 11/1981 | Parks |
| 4,416,280 A | 11/1983 | Carpenter et al. |
| 4,416,281 A | 11/1983 | Cooper et al. |
| 4,546,759 A | 10/1985 | Solar |
| RE32,057 E | 12/1985 | LeVeen |
| RE32,066 E | 1/1986 | Leveen |
| 4,583,969 A | 4/1986 | Mortensen |
| 4,662,383 A | 5/1987 | Sogawa et al. |
| 4,672,962 A | 6/1987 | Hershenson |
| 4,676,258 A | 6/1987 | Inokuchi et al. |
| 4,707,587 A | 11/1987 | Greenblatt |
| 4,745,922 A | 5/1988 | Taylor |
| 4,748,979 A | 6/1988 | Hershenson |
| 4,750,493 A | 6/1988 | Brader |
| 4,754,752 A | 7/1988 | Ginsburg et al. |
| 4,759,349 A | 7/1988 | Betz et al. |
| 4,791,930 A | 12/1988 | Suzuki et al. |
| 4,813,210 A | 3/1989 | Masuda et al. |
| 4,819,655 A | 4/1989 | Webler |
| 4,823,076 A | 4/1989 | Haines et al. |
| RE32,983 E | 7/1989 | Levy |
| 4,844,074 A | 7/1989 | Kurucz |
| 4,846,177 A | 7/1989 | Leonard |
| 4,850,958 A | 7/1989 | Berry et al. |
| 4,860,744 A | 8/1989 | Johnson et al. |
| 4,883,455 A | 11/1989 | Leonard |
| 4,899,741 A | 2/1990 | Bentley et al. |
| 4,920,963 A | 5/1990 | Brader |
| 4,941,475 A | 7/1990 | Williams et al. |
| 4,987,896 A | 1/1991 | Nakamatsu |
| RE33,561 E | 3/1991 | Levy |
| 5,011,468 A | 4/1991 | Lundquist et al. |
| 5,019,075 A | 5/1991 | Spears et al. |
| 5,021,045 A | 6/1991 | Buckberg et al. |
| 5,037,383 A | 8/1991 | Vaslef et al. |
| 5,041,089 A | 8/1991 | Mueller et al. |
| 5,059,167 A | 10/1991 | Lundquist et al. |
| 5,066,578 A | 11/1991 | Wikman-Coffelt |
| 5,078,713 A | 1/1992 | Varney |
| 5,092,841 A | 3/1992 | Spears |
| 5,098,376 A | 3/1992 | Berry et al. |
| 5,098,429 A | 3/1992 | Sterzer |
| 5,106,360 A | 4/1992 | Ishiwara et al. |
| 5,135,474 A | 8/1992 | Swan et al. |
| 5,139,496 A | 8/1992 | Hed |
| 5,147,355 A | 9/1992 | Friedman et al. |
| 5,147,385 A | 9/1992 | Beck et al. |
| 5,149,321 A | 9/1992 | Klatz et al. |
| 5,151,100 A | 9/1992 | Abele et al. |
| 5,158,534 A | 10/1992 | Berry et al. |
| 5,174,285 A | 12/1992 | Fontenot |
| 5,182,317 A | 1/1993 | Winters et al. |
| 5,190,540 A | 3/1993 | Lee |
| 5,191,883 A | 3/1993 | Lennox et al. |
| 5,196,024 A | 3/1993 | Barath |
| 5,207,640 A | 5/1993 | Hattler |
| 5,211,631 A | 5/1993 | Sheaff |
| 5,230,862 A | 7/1993 | Berry et al. |
| 5,234,405 A | 8/1993 | Klatz et al. |
| 5,248,312 A | 9/1993 | Langberg |
| 5,250,070 A | 10/1993 | Parodi |
| 5,257,977 A | 11/1993 | Eshel |
| 5,261,399 A | 11/1993 | Klatz et al. |
| 5,261,411 A | 11/1993 | Hughes |
| 5,262,451 A | 11/1993 | Winters et al. |
| 5,269,758 A | 12/1993 | Taheri |
| 5,271,743 A | 12/1993 | Hattler |
| 5,275,595 A | 1/1994 | Dobak, III et al. |
| 5,279,598 A | 1/1994 | Sheaff |
| 5,281,213 A | 1/1994 | Milder et al. |
| 5,281,215 A | 1/1994 | Milder |
| 5,304,214 A | 4/1994 | DeFord et al. |
| 5,324,286 A | 6/1994 | Fowle |
| 5,338,770 A | 8/1994 | Winters et al. |
| 5,342,301 A | 8/1994 | Saab |
| 5,342,693 A | 8/1994 | Winters et al. |
| 5,346,508 A | 9/1994 | Hastings |
| 5,348,554 A | 9/1994 | Imran et al. |
| 5,354,277 A | 10/1994 | Guzman et al. |
| 5,383,856 A | 1/1995 | Bersin |
| 5,395,314 A | 3/1995 | Klatz et al. |
| 5,403,281 A | 4/1995 | O'Neill et al. |
| 5,405,322 A | 4/1995 | Lennox |
| 5,411,477 A | 5/1995 | Saab |
| 5,423,807 A | 6/1995 | Milder |
| 5,437,673 A | 8/1995 | Baust et al. |
| 5,452,582 A | 9/1995 | Longsworth |
| 5,460,628 A * | 10/1995 | Neuwirth et al. ............. 606/28 |
| 5,464,437 A | 11/1995 | Reid et al. |
| 5,478,309 A | 12/1995 | Sweezer et al. |
| 5,486,204 A | 1/1996 | Clifton |
| 5,486,208 A | 1/1996 | Ginsburg |
| 5,531,776 A | 7/1996 | Ward et al. |
| 5,542,928 A | 8/1996 | Evans et al. |
| 5,545,161 A | 8/1996 | Imran |
| 5,549,559 A | 8/1996 | Eshel |
| 5,562,606 A | 10/1996 | Huybregts |
| 5,571,153 A * | 11/1996 | Wallsten ...................... 607/98 |
| 5,609,591 A | 3/1997 | Daikuzono |
| 5,609,620 A | 3/1997 | Daily |
| 5,624,392 A | 4/1997 | Saab |
| 5,655,548 A | 8/1997 | Nelson et al. |
| 5,656,420 A | 8/1997 | Chien |
| 5,693,080 A | 12/1997 | Wallsten et al. |
| 5,702,435 A | 12/1997 | Maytal |
| 5,716,386 A | 2/1998 | Ward et al. |
| 5,733,319 A | 3/1998 | Neilson et al. |
| 5,735,809 A | 4/1998 | Gorsuch |
| 5,758,505 A | 6/1998 | Dobak, III et al. |
| 5,759,182 A | 6/1998 | Varney et al. |
| 5,787,715 A | 8/1998 | Dobak, III et al. |
| 5,797,948 A | 8/1998 | Dunham |
| 5,800,375 A | 9/1998 | Sweezer et al. |
| 5,800,486 A | 9/1998 | Thome et al. |
| 5,807,395 A | 9/1998 | Mulier et al. |
| 5,827,269 A * | 10/1998 | Saadat ........................ 606/28 |
| 5,837,003 A | 11/1998 | Ginsburg |
| 5,861,021 A | 1/1999 | Thome et al. |
| 5,868,735 A | 2/1999 | Lafontaine |
| 5,871,526 A | 2/1999 | Gibbs et al. |
| 5,876,667 A | 3/1999 | Gremel et al. |
| 5,879,316 A | 3/1999 | Safar et al. |
| 5,879,347 A | 3/1999 | Saadat |
| 5,899,899 A | 5/1999 | Arless et al. |
| 5,902,268 A | 5/1999 | Saab |
| 5,902,299 A | 5/1999 | Jayaraman |
| 5,906,588 A | 5/1999 | Safar et al. |
| 5,957,917 A | 9/1999 | Doiron et al. |
| 5,957,963 A | 9/1999 | Dobak, III |
| 5,975,081 A | 11/1999 | Hood et al. |
| 6,019,783 A | 2/2000 | Philips et al. |
| 6,033,383 A | 3/2000 | Ginsburg |
| 6,042,559 A | 3/2000 | Dobak, III |

| | | |
|---|---|---|
| 6,110,168 A | 8/2000 | Ginsburg |
| 6,126,684 A | 10/2000 | Gobin et al. |
| 6,146,411 A | 11/2000 | Noda et al. |
| 6,190,356 B1 | 2/2001 | Bersin |
| 6,299,599 B1 | 10/2001 | Pham et al. |
| 6,338,727 B1 | 1/2002 | Noda et al. |

OTHER PUBLICATIONS

U.S. patent application Ser. No. 09/349,606, Balding, pending.

U.S. patent application Ser. No. 09/413,752, Evans et al., pending.

U.S. patent application Ser. No. 09/413,753, Evans et al., pending.

U.S. patent application Ser. No. 09/456,110, Luo et al., pending.

U.S. patent application Ser. No. 09/477,490, Lasersohn et al., pending.

U.S. patent application Ser. No. 09/494,896, Philips et al., pending.

U.S. patent application Ser. No. 09/498,499, Worthen, pending.

U.S. patent application Ser. No. 09/503,014, Gobin et al., pending.

U.S. patent application Ser. No. 09/540,693, Worthen et al., pending.

U.S. patent application Ser. No. 09/546,814, Gobin et al., pending.

U.S. patent application Ser. No. 09/565,039, Worthen et al., pending.

U.S. patent application Ser. No. 09/761,069, Whitebook et al., pending.

* cited by examiner

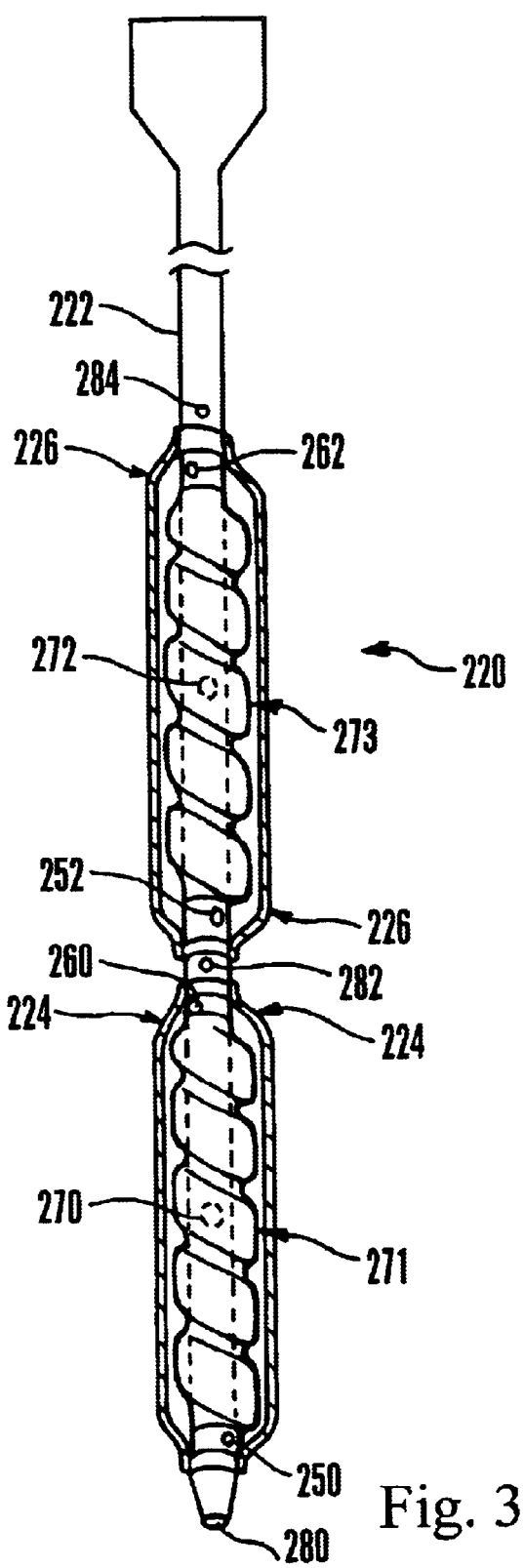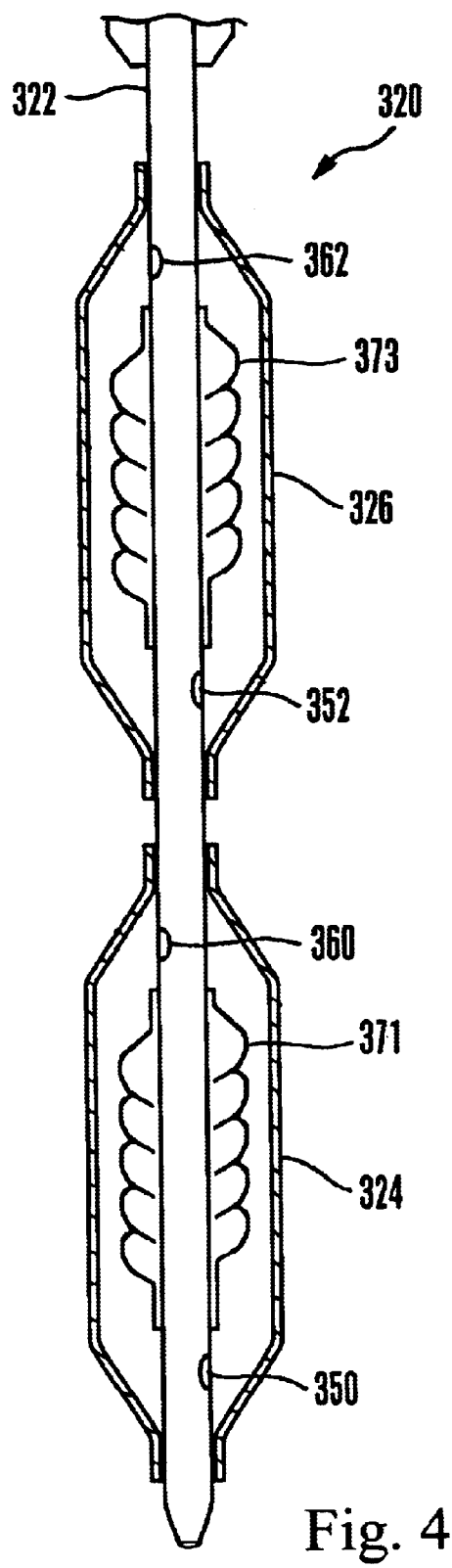
Fig. 3
Fig. 4

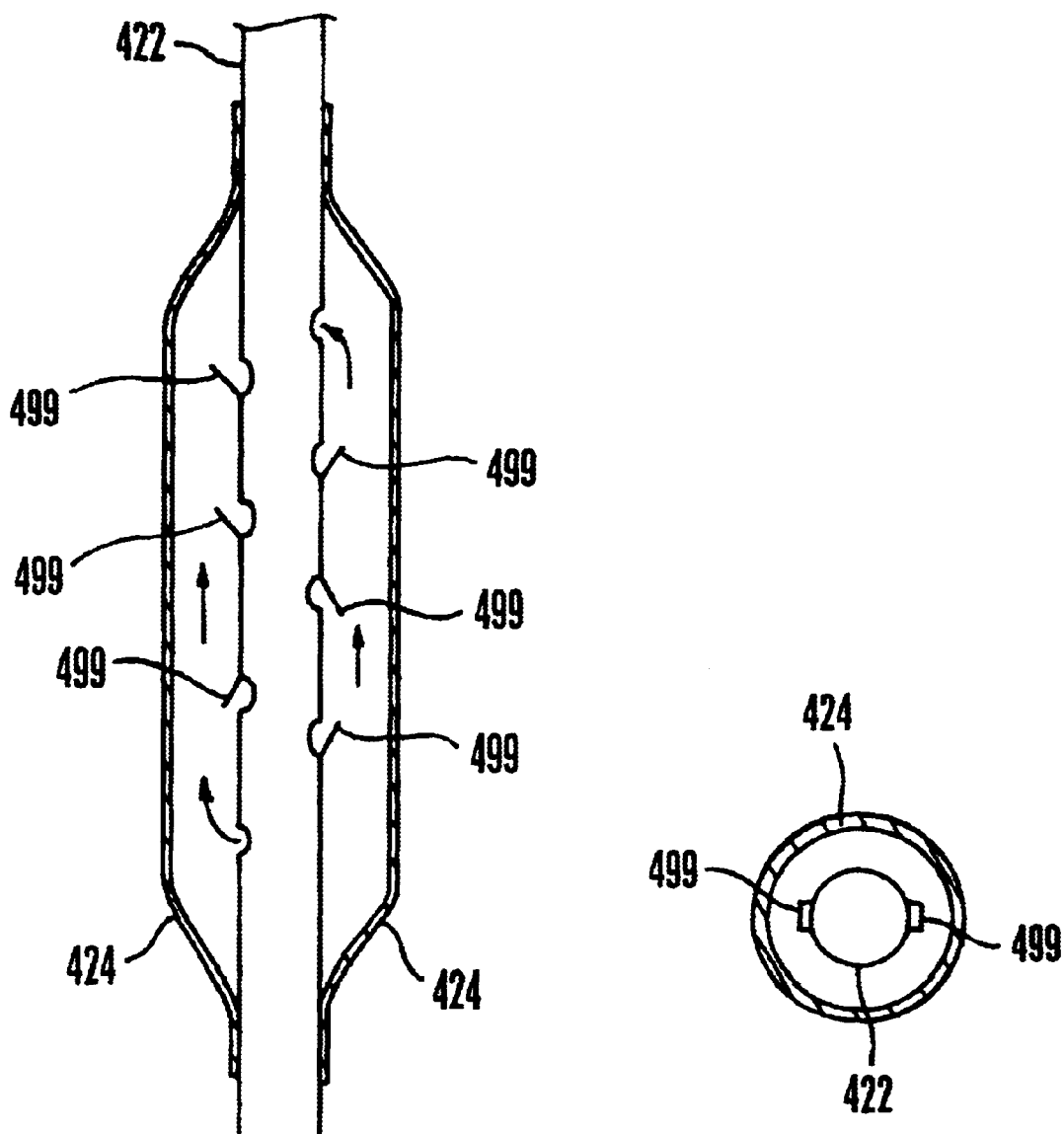

INTRAVASCULAR CATHETER WITH HEAT EXCHANGE ELEMENT HAVING INNER INFLATION ELEMENT AND METHODS OF USE

CROSS-REFERENCE TO RELATED APPLICATIONS

This application is a continuation-in-part of, and claims priority to, patent application Ser. No. 09/503,014, filed Feb. 11, 2000 now U.S. Pat. No. 6,409,747 and entitled Indwelling Heat Exchange Catheter and Method of Using Same which is a continuation of patent application Ser. No. 09/063,984, filed on Apr. 21, 1998 and entitled Indwelling Heat Exchange Catheter and Method of Using Same, now issued as U.S. Pat. No. 6,126,684 which are hereby incorporated by reference in their entirety.

BACKGROUND OF THE INVENTION

The field of the present invention is apparatus and methods for producing heat exchange with a body fluid flowing through a body conduit of a patient.

Catheters such as central venous line catheters are typically used in ICU (intensive care unit) patients, particularly in those patients who have suffered a stroke or other brain traumatic event. Central venous line catheters are typically about 5 to 12 French in size and have a flexible multi-lumen elongate body extending 6 to 12 inches. They may be introduced through the subclavian or jugular veins, or through the femoral vein of the patient, serving to provide the caretaker with easy and convenient access to the patient's central blood supply via the central venous system. In this manner general access to the central blood supply is gained, enabling, for example, delivery of drugs, infusion fluids or nutrition, along with the gathering of patient blood for blood gas analysis and the like.

In certain medical circumstances, such as in the case of a stroke patient or other brain trauma patient, it may be desirable to rapidly reduce the patient's body temperature. For example, fever, which is common in neuro-ICU patients, may exacerbate detrimental effects in the brain. It may be desireable to reduce the body temperature of a patient having a fever to a normal body temperature.

In some cases such as but not limited to, cardiac surgery, beating heart surgery, coronary arterial bypass graft (CABG) procedure, acute myocardial infarction procedure, aneurysm procedure etc., it is sometimes considered desirable to reduce the patient's body temperature below normal body temperature so that the patient experiences hypothermia. Many advantages of hypothermia are known. By way of example, it has been found desirable to lower the temperature of body tissue in order to reduce the metabolism of the body. This has been particularly desirable in surgical applications where the reduced metabolism has made it possible to more easily accommodate lengthy operative procedures. In cases of stroke and several other pathological conditions, hypothermia also reduces the permeability of the blood/brain barrier. It inhibits release of damaging neurotransmitters and also inhibits calcium-mediated effects. Hypothermia also inhibits brain edema and lowers intracranial pressure.

Conventional therapies to cool a patient include treatment with acetaminophen (Tylenol), cooling blankets, ice water bladder lavages, and ice baths. These approaches to cooling a patient require excessive cooling time and do not provide for precise control of patient cooling.

In other medical situations, it may be desirable to maintain the patient's body at normothermia when the body's metabolic tendency is to drift below normal temperature of about 98.6° F. (37° C.), or it may be desirable to raise the patient's body temperature once it has drifted below normal back to normothermia. For example, a patient may suffer from unintended hypothermia and may need to be warmed to a normothermic temperature, e.g., 98.6° F. (37° C.). These results can be obtained by intravascular heating. The catheters disclosed herein may be used in connection with heating/cooling systems that are disclosed in U.S. Pat. Nos. 6,019,783 and 6,146,411 which are hereby incorporated by reference as if fully set forth herein. If the desire is to cool a hyperthermic patient as quickly as possible, the system's heat exchange capacity should be set to its coldest temperature setting, for example a system bath temperature of about 0° C. If the desire is to warm a hypothermic patient back to normothermia as quickly as possible, the system's heat exchange capacity should be set to its hottest temperature setting, for example a system bath temperature of about 49° C.

To minimize the number of incisions and catheter insertions into the patient's body and cool or heat the patient relatively quickly and in a controlled fashion, a central venous catheter may be configured to include a cooling or a heating exchange capability.

By supplementing the known functions of a central venous line catheter with the function of cooling or warming the patient's blood, a catheter may take advantage of existing access to the venous system using a single, relatively small incision, reducing the risk of additional complications. The access, typically through the subclavian, jugular or femoral veins, is to the central blood supply, via the central venous system, and is therefore particularly expedient, permitting efficient cooling or warming of a patient. The term central venous system generally relates to the portion of the venous system which returns blood to the right side of the heart, including the inferior and superior vena cava.

A catheter having one or more lumens may be inserted into a blood vessel of a patient to deliver medication, collect blood for analysis, and the like. A separate lumen may be provided for transporting a heat exchange fluid, e.g., cold, warm or hot water or saline. The fluid may circulate via the lumen and through a thin-walled inflated balloon formed on the surface of the catheter. The fluid exchanges heat with the blood in the blood vessel via the thin walls of the balloon. Outside the patient's body, the fluid passes through a cooling or heating system to re-cool or re-heat the fluid. Such a catheter may lower or raise the temperature of the patient's blood and, as described above, may thereby improve the patient's medical condition.

It would be advantageous to provide a heat exchange catheter that maximizes intravascular cooling and heating without compromising physiological conditions, and facilitates access to the patient's blood stream, thereby overcoming one or more problems associated with the related art.

BRIEF SUMMARY OF THE INVENTION

The present invention is directed to a heat exchange catheter and method for its use. A heat exchange element is combined with an infusion lumen to provide efficient cooling (and/or heating) and access to the patient's blood steam.

In a first separate aspect of the invention, a heat exchange catheter comprises a generally tubular elongate body defining lumens through which one or more fluids may flow, at least one heat exchange element disposed about an implantable portion of the catheter, and at least one inflation element disposed within the heat exchange element. A fluid fills the inflation element and the same or a different fluid circulates through the heat exchange element.

In a second separate aspect of the invention, a heat exchange catheter comprises a generally tubular elongate body defining an inflow lumen and an outflow lumen. The inflow lumen supplies heat exchange fluid to at least one heat exchange element disposed about an implantable portion of the catheter and at least one inflation element disposed within the heat exchange element. The heat exchange fluid exits the heat exchange element and flows into the outflow lumen such that fluid may circulate through the heat exchange element via the inflow lumen and outflow lumen.

In a third separate aspect of the invention, a heat exchange catheter comprises a generally tubular elongate body defining an inflow lumen, an outflow lumen and an inflation lumen. The inflow and outflow lumens circulate heat exchange fluid within at least one heat exchange element disposed about an implantable portion of the catheter. The inflation lumen supplies inflation fluid to at least one inflation element disposed within the heat exchange element.

In a fourth separate aspect of the invention, at least one inflation element is configured to promote mixing of the heat exchange fluid as it flows between the inflation element and the heat exchange element.

In a fifth separate aspect of the invention, the generally tubular elongate body further defines at least one infusion lumen that provides access to the central blood supply of the patient.

In a sixth separate aspect of the invention, a heat exchange catheter is provided with multiple infusion lumens (preferably three to five infusion lumens) with infusion ducts separated along the catheter at spaced intervals, such that the catheter may be used to simultaneously introduce various fluids, such as medications, into the patient at different points in the patient's blood stream, so as to avoid mixing incompatible fluids in excessive concentrations.

In a seventh separate aspect of the invention, the elongate body further defines a guidewire lumen that accommodates a guidewire that may be used to assist insertion of the catheter.

In an eighth separate aspect of the invention, a heat exchange element and/or the elongate body has an irregular surface that promotes mixing of, or disturbs the flow of, heat exchange fluid as the fluid flows through the heat exchange element.

In a ninth separate aspect of the present invention, it is contemplated that combinations of the foregoing separate aspects may be incorporated into a single embodiment.

Therefore, it is an object of the present invention to provide an improved heat exchange catheter and a method for its use. Other and further objects and advantages will appear hereafter.

BRIEF DESCRIPTION OF THE DRAWINGS

FIG. 3 is a schematic side elevational view of a third embodiment of an intravenous catheter;

FIG. 4 is a schematic side elevational view of a distal portion of a fourth embodiment of an intravenous catheter;

FIG. 5 is a schematic side elevational view of a distal portion of a fifth embodiment of an intravenous catheter;

FIG. 5A is a schematic cross-sectional view of the intravenous catheter of FIG. 5.

DETAILED DESCRIPTION OF THE INVENTION

Figure 1:
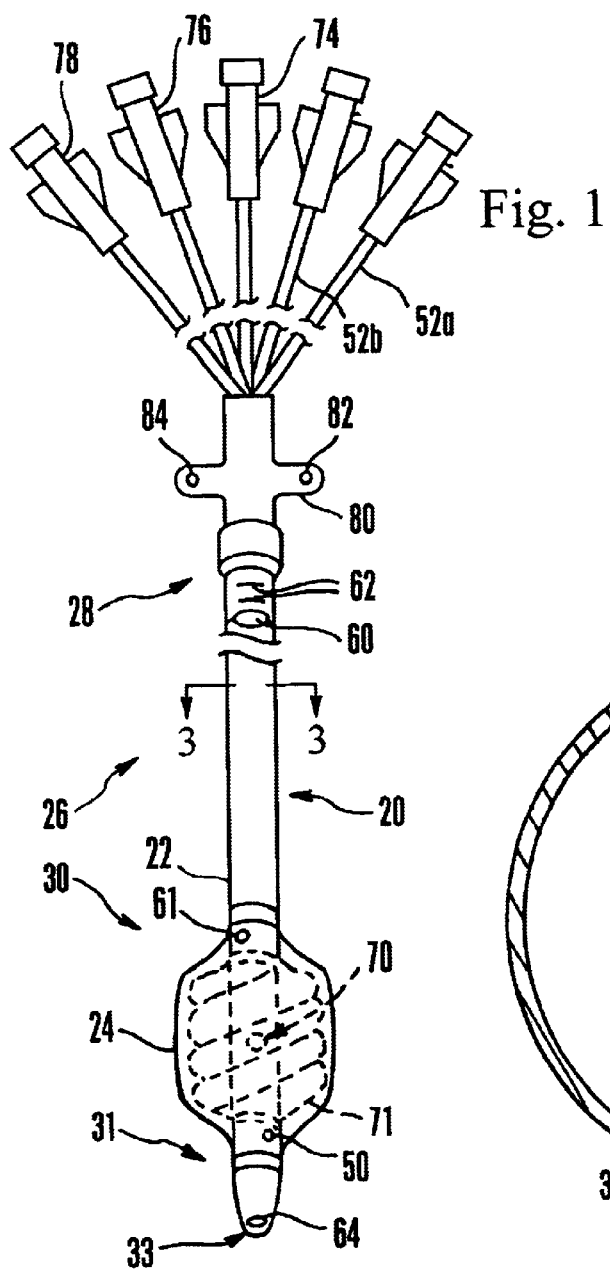
FIG. 1 is a schematic side elevational view of a first embodiment of an intravenous catheter.

The preferred embodiments will be described with reference to drawing figures, wherein like reference numerals are applied to like elements.

U.S. Pat. Nos. 6,146,411, 6,126,684, and 6,165,207 each of which is hereby incorporated by reference, disclose systems employing catheters that may be inserted into the body of a patient to exchange heat with the blood supply of the patient.

Figure 1A:
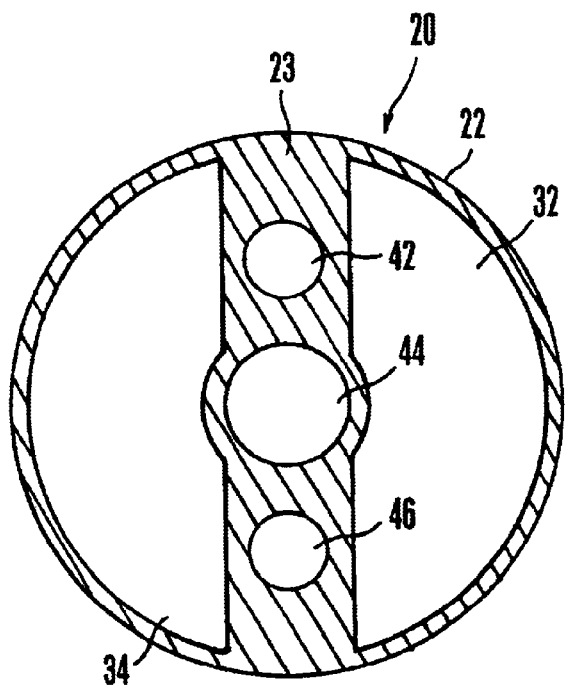
FIG. 1A is a cross-sectional view of the intravenous catheter of FIG. 1.

FIGS. 1 and 1A depict one embodiment of an intravascular catheter 20 adapted to exchange heat with a body fluid flowing through a body conduit of a patient. The catheter 20 comprises an elongate body 22 having a substantially tubular configuration, a proximal portion 26 with a proximal end 28, and a distal portion 30 with a distal end 31. When operatively disposed, the distal end 31 is disposed within the patient's body, and the proximal end 28 is disposed outside of the patient's body.

At least one heat exchange element 24, such as a fluid-carrying inflatable balloon, extends at least partially along the implantable, distal portion 30 of the elongate body 22. For illustrative purposes, this embodiment is shown to have only one heat exchange element 24. Preferably, however, a catheter has more than one heat exchange element, as will be described below in connection with other embodiments, and may have any number of heat exchange elements.

Preferably, an inner inflation element 71 is contained within the heat exchange element 24. The inflation element 71 preferably comprises an inflatable balloon that may be moved between a deflated configuration in which the balloon lies substantially against the elongate body 22 of the catheter 20 and an inflated configuration in which the balloon is expanded away from the elongate body 22. The inner inflation element 71 may be a smaller version of the heat exchange element 24. In one embodiment, the inner inflation element 71 is a spiral shaped balloon.

Alternately, rather than employing a compliant inflation element that may be inflated from a substantially flattened congifuration to an expanded configuration, the inflation element may include a rigid inner balloon that remains in an inflated configuration.

Heat exchange fluid (not shown) preferably flows through the elongate body and through the heat exchange element 24 to heat or cool a patient. The heat exchange fluid is remotely cooled or heated outside of the catheter 20, such as by a temperature control system (not shown), and is conveyed between the catheter 20 and, for example, a temperature control system, via an inlet tube 52a and an outlet tube 52b.

Referring also to FIG. 1A, which is a cross-sectional view of the catheter 20 of FIG. 1, the elongate body 22 of this embodiment comprises an inflow lumen 32, an outflow lumen 34, an inflation lumen 42 and two auxiliary lumens 44 46. External access to the inflation lumen 42 and two auxiliary lumens 44 46 is supplied by infusion lumen fittings 74, 76, 78.

Heat exchange fluid is supplied through the inflow lumen 32 and enters the heat exchange element 24 through the inflow duct 50. The heat exchange fluid flows through the cavity between the heat exchange element 24 and the inflation element 71, and exits the cavity through the outflow duct 61.

The particular heat exchange fluid selected is preferably biocompatible to avoid harm to the patient in the event of inadvertent rupture. Candidate materials include sterile saline and water, although other fluids having suitable viscosity, heat exchange and material compatibility characteristics can also be used.

The inflation element 71 is inflated with a fluid (liquid or gas). The fluid used to inflate the inflation element 71 preferably is an inflation fluid that is separate from the heat exchange fluid that circulates through the heat exchange element 24. Separating the fluids permits the fluids to be at different pressures so that the degree of inflation can be controlled independently of the flow of the heat exchange fluid. Inflation fluid is supplied to the inflation element 71 from an inflation lumen 42 through an inflation duct 70. Although the inflation fluid and heat exchange fluid in such embodiments are separated within the catheter 20, the fluids may actually be the same substance (e.g., saline) and may be mixed outside of the catheter 20.

Figure 2:
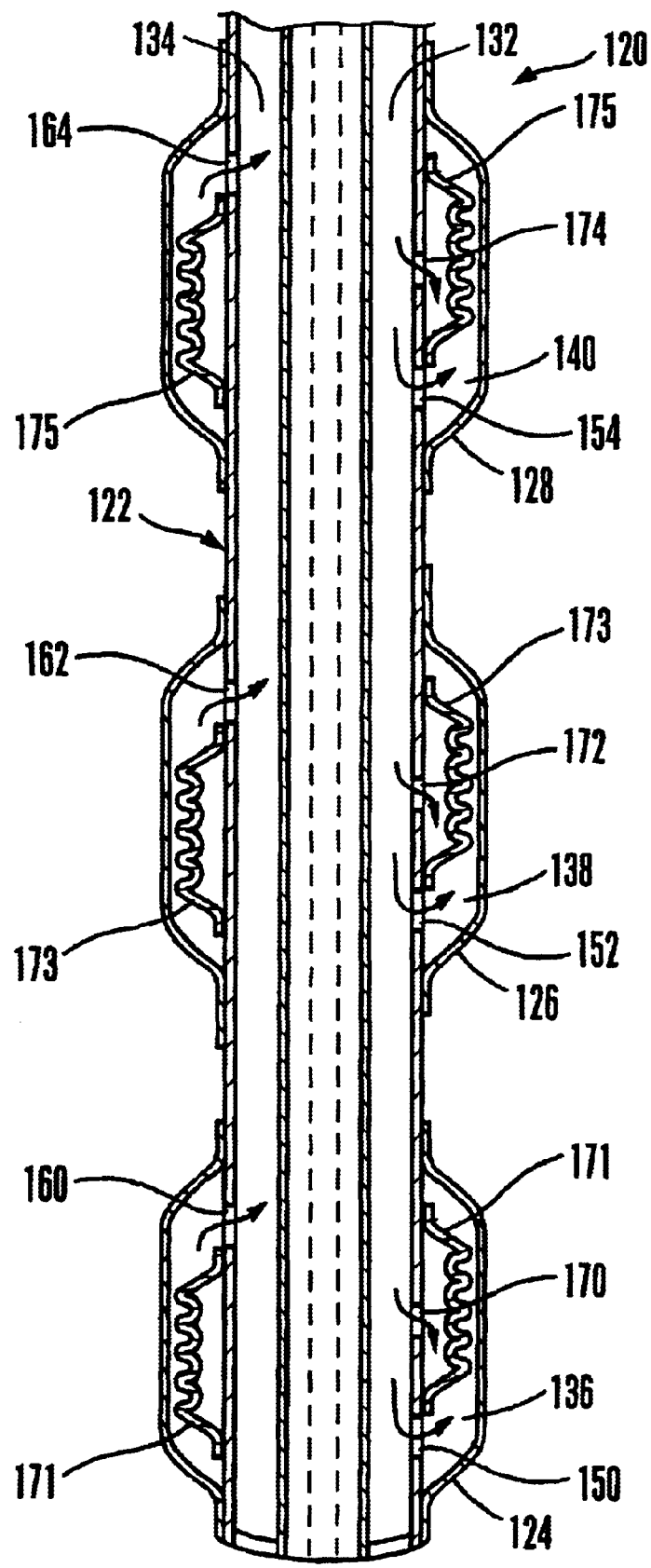
FIG. 2 is a schematic sectional view of a distal portion of a second embodiment of an intravenous catheter.

Alternately, as shown in FIG. 2, an inflation element 171 may be inflated with heat exchange fluid that is supplied to the inflation element 171 from the inflow lumen 132 through the inflation duct 170. In such embodiments, the inflow lumen 132 supplies heat exchange fluid to both the inflation element 171 and the heat exchange element 124.

Again referring to FIGS. 1 and 1A, there alternately may be no inflow duct 70 providing direct fluid communication between the inflow lumen 32 and the heat exchange element 24. The inflation element 71 may have an orifice (not shown) providing fluid communication between the inflation element 71 and the heat exchange element. The heat exchange fluid may flow into the inflation element 71 through the inflation duct 70, and flow from the inflation element 71 into the heat exchange element 24 via the orifice in the inflation element 71.

The auxillary lumens 44 46 may serve a multiplicity of functions, including infusion of various drugs such as but not limited to chemotherapy, fluids and nutrition, guidewire support, access to syringes for sampling, and accommodation of various sensors, such as thermistors to monitor the patient, thus generally providing access to the central blood supply as dictated by the particular application. Each auxillary lumen 44, 46 preferably has an infusion duct (not shown) for providing fluid communication between the auxiliary lumen 44 46 and the body conduit in which the catheter 20 is intubated.

The inflation lumen 42 and auxillary lumens 44 46 may have different diameters. For example, the central lumen 44 may have a larger diameter than the other lumens 42 46 in order to better support a guidewire for instance. While the catheter 20 depicted in FIG. 1 has an inflation lumen 42 and two auxiliary lumens 44 46, other numbers of such lumens are contemplated and may be suitable depending on the particular application.

In embodiments that do not use an inflation lumen 42 to inflate the inflation element 71 (such as catheters as shown in FIG. 2 that use the inflow lumen 134 to inflate the inflation element 171), the lumen that may otherwise serve as the inflation lumen 42 may instead be configured as an auxiliary lumen.

The catheter 20 preferably is formed of a polymer material 23 that defines the various lumens 32, 34, 42, 44 and 46.

A preferred material 23 is polyurethane, although other materials, such as nylon, polyethylene, PEBAX, PVC, Tygon® or the like can also be used. Considerations in selecting the appropriate material 23 include biocompatibility, flexibility, temperature change compatibility, and resistance to buckling.

Various balloon configurations for both the heat exchange element 24 and the inflation element 71 may be employed, including but not limited to straight, helical, cylindrical, and fluted shapes. The particular configurations selected depends on the application and the desired heat exchange and other characteristics.

The rate of heat transfer depends on such factors as the volumetric flow rates of the blood and the heat exchange fluid, and the temperature difference between the heat exchange element 24 and the blood. Other factors include the convection heat transfer coefficient of the two fluids involved in the heat exchange, the thermal conductivity and thickness of the barrier between the two fluids, and the residence time of the heat transfer. Increasing the cooling or heating rate may be accomplished by, for example, increasing the size (diameter and/or length) of the heat exchange element 24, increasing the temperature difference between the heat exchange fluid and the blood, or increasing the pump rate of the heat exchange fluid.

Increasing the diameter of the heat exchange element 24, however, may result in blocking the flow of blood in the blood vessel, and/or may cause thrombosis. Increasing the size of the heat exchange element 24 is further complicated by the fact that the size of blood vessels may vary widely among different patients. A catheter 20 that maximizes heat transfer for a larger patient may be too large for use in a smaller patient, and a catheter 20 that maximizes heat transfer for a smaller patient may not maximize heat transfer in a larger patient. For example, a relatively large heat exchange element 24 may excessively block blood flow through a smaller patient's blood vessel, increasing the risk of thrombosis. Further, a tip of a relatively large catheter 20 designed for a larger patient, if inserted completely into a smaller patient's upper central venous system, may extend into the patient's heart.

Increasing the temperature difference between the heat exchange fluid and the blood excessively may lead to undesireable effects, such as thermal damage to the blood vessel wall. Further, blood has a maximum desirable heating limit because above certain termperatures blood proteins may degenerate and coagulation may occur. This limits the maximum operating temperature of known intravascular catheters.

The rate of heat transfer may also depend partially on the geometry of the heat exchange element 24. Because the operating temperature of an intravascular catheter is limited, the catheter geometry may take on increased importance to effectuate heat transfer. The flow of the heat exchange fluid inside a heat exchange element may typically be substantially laminar, and the flow of the patient's blood over a heat exchange element may also typically be substantially laminar, such that much of the heat exchange occurs between only portions of the heat exchange fluid and blood that are nearest the heat exchange element surfaces.

Heat exchange is enhanced when the heat exchange fluid is provided with well mixed flow. Mixing can be enhanced by providing an irregular surface next to which the heat exchange fluid flows. To promote mixing or disturbance of the flow paths of the heat exchange fluid and the patient's blood, a heat exchange balloon may be configured in a helical (referred to interchangeably herein as "spiral") shape, or otherwise configured, such that the heat exchange balloon disturbs both the flow of the heat exchange fluid inside the balloon and the flow of the blood outside the balloon, increasing the rate of heat transfer.

In some situations, it might be desireable to configure a catheter in a manner so as not to promote mixing of and/or turbulence in the blood flowing outside the heat exchange balloon, while promoting mixing of the heat exchange fluid flowing within the heat exchange balloon for more efficient heat exchange.

Preferably, the heat exchange element 24 has a substantially straight configuration to inhibit coagulum from forming on the catheter and to minimize turbulence and shear which may be undesirable in a particular application.

To enhance mixing of the heat exchange fluid flowing inside the heat exchange element 24, the inflation element 71 preferably has a spiral or helical configuration that turns or wraps in a spiral or helix about the elongate body 22 of the catheter 20 as shown in FIG. 1. A helical inflation element 71 enhances mixing of the heat exchange fluid outside the balloon, increasing the heat exchange rate and distributing the heat transfer more evenly throughout the heat exchange fluid.

Because the inner inflation element 71 is contained within a substantially straight heat exchange element 24 and does not contact the patient's blood, mixing is encouraged within the heat exchange element to increase cooling and/or heating capability, but mixing is minimized outside the heat exchange element 24. In a separate embodiment, using a spiral heat exchange element in contact with the blood would promote mixing both of the blood and the heat exchange fluid.

Configurations other than spiral or helical may also be employed to promote mixing. Any configuration having an irregular surface, as opposed to a smooth and straight surface, will promote mixing to some degree.

Additionally, the inflation element may have holes, skives, protrusions or an irregular surface that promotes mixing of the heat exchange fluid as it flows over the holes, skives, protrusions or otherwise irregular surface.

In addition to promoting mixing, the use of an inflation element inside a heat exchange element also reduces the volume of heat exchange fluid within the heat exchange element.

One or more depth markings 60, 62 may be disposed on the elongate body 22 to indicate the length of a portion of the catheter 20 that is intubated into the patient. Preferably, the depth markings 60, 62 are disposed at least on the proximal portion 26 of the elongate body 22 so that they are visible when the catheter 20 is intubated into the patient. The markings 60, 62 preferably indicate a length of the catheter 20 measured from each marking 60, 62 to the distal tip 33 of the catheter 20 and may be disposed at spaced intervals, such as one-centimeter intervals. Each marking 60, 62 may comprise any symbol that may be understood to represent a length or relative length or degree of intubation. One marking 60 is shown to comprise a numeral indicative of length (in centimeters, for example) from the marking 60 to the distal tip 33 of the catheter. Other markings 62 may comprise dots, lines, hash marks or other marks.

The elongate body 22 may also include a distal indicator 64 that indicates the position of the distal end 31 or distal tip 33 of the elongate body 22. The distal indicator 64 preferably is disposed near the distal tip 33 of the elongate body 22. The position of the distal indicator 64 inside the patient preferably may be determined using conventional medical technology, such as with X-ray technology. Information regarding the position of the distal end 31 or distal tip 33 of the elongate body 22 may aid proper placement of the catheter 20, so that the catheter 20 is inserted to a degree that maximizes the heat transfer rate without compromising physiological effects.

The catheter 20 preferably includes an anchor configured for affixing the catheter 20 to the patient. As shown in FIG. 1, the anchor may comprise a suture fitting 80. The suture fitting 80 can be made integrally with the catheter 20, or it can be made as a separate plastic fitting and engaged with the catheter 20. The suture fitting 80 includes two eyes 82, 84 through which sutures can be inserted and engaged with the patient or with a bandage or tape or other structure that is engaged with the patient. An anchor may be especially desirable in cases in which the catheter is intubated for an extended period.

A catheter may be provided with various numbers of heat exchange elements and inflation elements. FIG. 2 depicts a distal portion of a catheter 120 having three heat exchange elements 124, 126, 128 and three inflation elements 171, 173, 175. The principles described herein apply to catheters having any number of heat exchange elements and inflation elements.

One advantage of a multiple heat exchange element configuration is that the flow and temperature of heat exchange fluid that circulates in the catheter can be more easily controlled along the catheter such that a more even and balanced transfer of heat can be achieved. Further, multiple heat exchange elements may provide an increased surface area relative to embodiments having a single heat exchange element. Another advantage of a multiple heat exchange elements design is the ability of the catheter to bend and flex when placed in a curved vasculature.

Each heat exchange element 124, 126, 128 defines with the elongate body 122 and each inflation element 171, 173, 175 a cavity 136, 138, 140. In this embodiment, each inflation element 171, 173, 175 is inflated by heat exchange fluid that enters each inflation duct 170, 172, 174 from the inflow lumen 132. Accordingly, an inflation lumen is not included in this embodiment. Heat exchange fluid (as indicated by the arrows in FIG. 2) inflates the inflation elements 171, 173, 175 via the inflow lumen 132, and also is circulated through the heat exchange elements 124, 126, 128 via the inflow lumen 132 and the outflow lumen 134.

The heat exchange fluid may be either relatively cold or relatively warm, depending on whether patient cooling or heating is desired. While in the cavity 136, 138, 140 of the heat exchange element 124, 126, 128, the heat exchange fluid serves to provide a cold or warm fluid on an inner surface of each heat exchange element 124, 126, 128. With a body fluid, such as blood, flowing exteriorly of the heat exchange element 124, 126, 128, heat transfer occurs across the heat exchange element 124, 126, 128, effectively cooling or heating the body of the patient. The temperature of the heat exchange fluid is remotely controlled in order to achieve a desired patient target temperature or temperature range.

The inflow lumen 132 serves as an inflow channel supplying the heat exchange elements 124, 126, 128 with heat exchange fluid which is circulated through the catheter 20, while the outflow lumen 134 serves as an outflow channel returning the heat exchange fluid from the heat exchange elements 124, 126, 128 to the catheter 120. The inflow lumen 132 also supplies the inflation elements 171, 173, 175 with heat exchange fluid (which serves as the inflation fluid in such an embodiment) through the inflation ducts 170, 172, 174.

Each of the heat exchange elements 124, 126, 128 and inflation elements 171, 173, 175, each of which preferably comprises a balloon, may be formed from a piece of flexible sheet material or extruded tubing formed into a molded balloon of the desired shape and size and then bound or otherwise fixed to the elongate body 122 to form each cavity 136, 138, 140. In one embodiment, each heat exchange element 124, 126, 128 and inflation elements 171, 173, 175 is made of urethane, nylon, or PET and is thin-walled, i.e., has a wall thickness of less than three mils, and more preferably less than one and one-half mils. Further, each heat exchange element 124, 126, 128 preferably is coated with an antimicrobial substance, as well as an anticlot substance, such as heparin.

Each heat exchange element 124, 126, 128 and inflation element 171, 173, 175 is preferably inflatable from a deflated configuration, wherein the balloon lies substantially flush with the elongate body 122 of the catheter 120, to an operational configuration, wherein the heat exchange fluid inflates each balloon. The deflated configuration facilitates insertion of the catheter 120 into the patient.

The elongate body 22 includes an inflow duct 150, 152 154 and an outflow duct 160, 162, 164 for each heat exchange element 124, 126, 128. Each inflow duct 150, 152, 154 is in fluid communication with the inflow lumen 132. Each outflow duct 160, 162, 164 is in fluid communication with the outflow lumen 134. Heat exchange fluid introduced into the inflow lumen 132 enters a cavity 136, 138, 140 of each heat exchange element 124, 126, 128 through an inflow duct 150, 152, 154, flows through the heat exchange element 124, 126, 128, exits the heat exchange element 124, 126, 128 through an outflow duct 160, 162, 164, and flows through the outflow lumen 134 toward the proximal end of the catheter 120.

In one embodiment, the inflow duct 150, 152, 154 of each heat exchange element 124, 126, 128 is positioned distally of the corresponding outflow duct 160, 162, 164 to provide countercurrent flow. In another embodiment, the inflow duct 150, 152, 154 of each heat exchange element 124, 126, 128 is positioned proximally to the corresponding outflow duct 160, 162, 164 to provide concurrent flow. Further information regarding the structure, functions, positions and relative sizes of inflow ducts and outflow ducts is disclosed in U.S. Pat. No. 6,126,684.

FIG. 3 depicts a catheter 220 having two heat exchange elements 224, 226 and inflation elements 271, 273. In this embodiment, an inflation lumen (not shown) supplies inflation fluid (which may be the same substance as the heat exchange fluid) to each inflation element 271, 273 through an inflation duct 270, 272. Use of an inflation lumen allows the inflation fluid flow to be controlled independently of the heat exchange fluid flow.

Heat exchange fluid is conveyed to the heat exchange elements 224, 226 through the inflow ducts 250, 252 and away from the heat exchange elements 224, 226 through the outflow ducts 260, 262. The catheter 220 preferably has multiple infusion ducts 280, 282, 284 to provide fluid communication between one or more infusion lumens and the patient. As shown, the infusion ducts 280, 282, 284 preferably are located in areas of the elongate body 222 that are not covered by a heat exchange element 224, 226 so that the infusion ducts 280, 282, 284 need not fluidly communicate through a heat exchange element 224, 226.

Providing multiple infusion ducts that are spaced apart on a catheter allows, for example, the simultaneously delivery different medications to the patient at different locations in the patient's bloodstream, which may be especially desirable where mixing of the medications (in relatively high concentrations) is desired to be avoided.

A catheter preferably has a size (e.g., length and diameter and/or cross-sectional area) that maximizes the heat transfer rate without causing harmful physiological effects. It is believed that in at least some blood vessels, flow of blood through the vessel begins to be reduced when approximately 50% of the blood vessel cross section is blocked. To maintain blood flow, the cross-sectional size (e.g., diameter and/or area) of the balloon, in combination with the cross-sectional size of the elongate body, preferably is no more than approximately 30% to 75% of the cross-sectional size of the blood vessel in which the balloon is inserted, which will vary with the size of each patient's vasculature. This range may be modified to provide a suitable safety margin.

Representative dimensions of a catheter 320 that would be appropriately sized for at least some patients is shown in FIG. 4. Each inflation element 371, 373 preferably has a shorter length than the corresponding heat exchange element 324, 326 so that a portion of the elongate body 322 is enclosed by the heat exchange element 324, 326 but not by the corresponding inflation element 371, 373 inside the heat exchange element 324, 326. Such a configuration provides space on the elongate body 322 for positioning the inflow ducts 350, 352 and the outflow ducts 360, 362 in a manner that the heat exchange fluid does not have to first flow through the inflation element 371, 373 before flowing into the heat exchange element 324, 326.

As shown in FIG. 4, a heat exchange element 326 having a length of approximately 3.169 cm and a diameter of approximately 5 mm was found to be suitable for use with an inflation element 373 having a length of approximately 2.330 cm and a diameter of approximately 4.44 mm, and a heat exchange element 324 having a length of approximately 1.968 cm and a diameter of approximately 8 mm was found to be suitable for use with an inflation element 371 having a length of approximately 1.350 cm and a diameter of approximately 7.48 mm. Other sizes would also be suitable.

In addition to or instead of using an inflation element, mixing of the heat exchange fluid may also be promoted by providing any irregular surface over which the heat exchange fluid flows through the heat exchange element 424, as example of which is shown in FIGS. 5 and 5A. For example, the elongate body 422 or the inner surface of the heat exchange element 424 may be provided with an irregular surface, which may include protrusions 499, divits and/or other obstructions. Such protrusions 499 may be made, for example, by skiving the surface of the elongate body 422 so that portions of the material forming the elongate body 422 are cut out of the elongate body 422 and bent away from the body 422.

Mixing might also be promoted by providing a coil of material (not shown) that wraps around the elongate body and obstructs the flow of the heat exchange fluid over the elongate body. As an additional example, a sleeve could be wrapped around and bonded to the elongate body. Interference with the smooth flow of the heat exchange fluid may be provided by a variety of irregular surfaces or configurations.

In accordance with a preferred method of use, the catheter may be inserted percutaneously through a puncture or surgical cut near the groin. Prior to insertion, the size (e.g., cross-section and/or length) of the body conduit in which the catheter is to be inserted may be measured, and a catheter may be selected based on the size of the body conduit, so that the catheter maximizes the heat transfer rate without deleterious physiological effects to the patient.

Preferably, the catheter is inserted into the patient with all of the inflation elements and/or heat exchange elements being deflated and lying substantially flush with the elongate body. In this deflated configuration, the catheter has a sufficiently small diameter to ease insertion of the catheter and avoid damaging the patient's venous system during insertion.

Following this initial introduction, the catheter may be inserted into the femoral and iliac veins, and the inferior vena cava (IVC), of a patient. In this embodiment, the catheter is inserted into blood vessels of the lower central venous system, such as the femoral and iliac veins and the inferior vena cava (IVC) where the volume of the lower central venous system is greater than that of the upper central venous system (jugular or subclavian, innominate, and superior vena cava), allowing a larger catheter (in both length and cross-sectional size) to be used. Alternately, however, the catheter systems disclosed herein may be used in the upper central venous system as may be preferred by some medical practitioner.

After the catheter is inserted and appropriately positioned in the patient, the inflation elements and the heat exchange elements may be inflated with heat exchange fluid and/or inflation fluid. Heat exchange fluid is circulated through the heat exchange element(s), preferably with the inflation elements and the heat exchange elements inflated.

With embodiments having a separate inflation lumen providing an inflation fluid to the inflation element, the pressure of the inflation fluid preferably may be varied to control the diameter of the inflation element. Higher pressure preferably expands the inflation element to a greater degree than lower pressure, decreasing the cross-sectional area of the space between the inflation element and the heat exchange element through which the heat exchange fluid may flow. Indeed, with adequate inflation pressure, the inflation element may touch the heat exchange element in some areas.

Due to the varying expansion of the inflation element, the heat transfer rate may vary as a function of inflation pressure. It may therefore be advantageus to use a separate inflation lumen to independently control the inflation pressure.

The heat exchange relationship between the catheter and the central venous system of the patient may be maintained for a prolonged duration—for example, from about one hour to about twenty-nine days.

Before removing the catheter from the patient, the inflation element preferably is deflated, such as by applying a suction to the lumen used to inflate the inflation element—either the inflation lumen or the inflow lumen, depending on the embodiment.

Figure 6A:
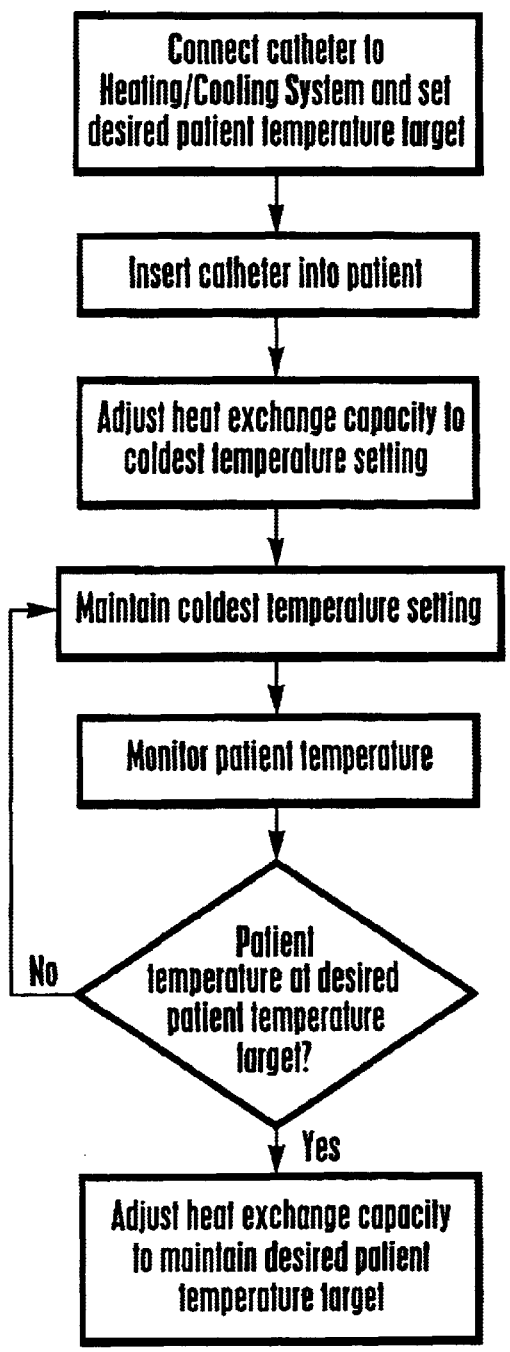
FIGS. 6A and 6B are flow diagrams for operating the present invention using a heating/cooling system.
Figure 6B:
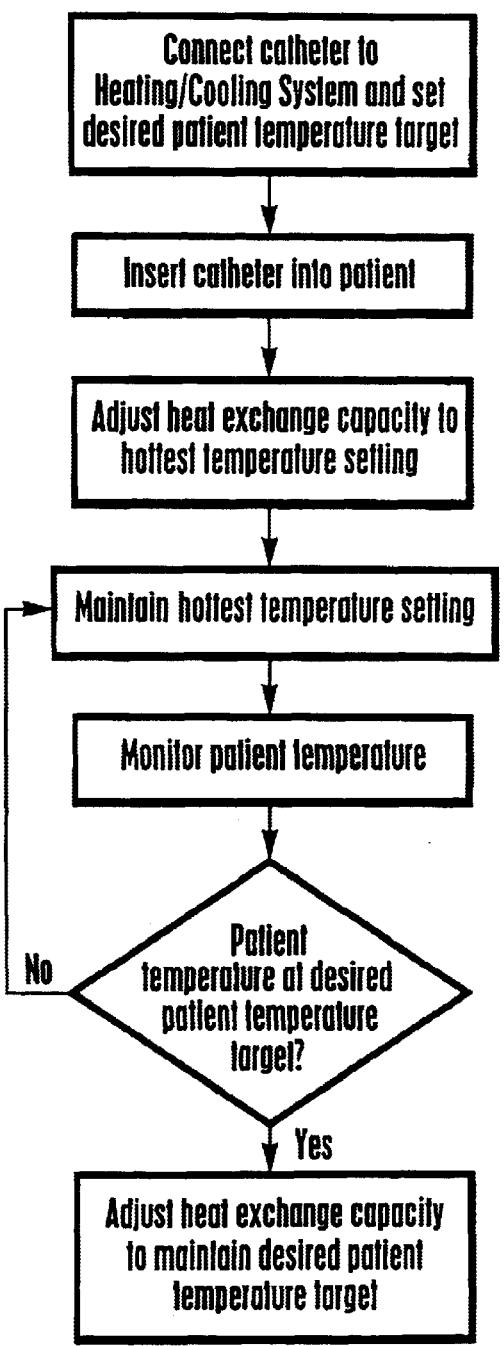

The catheter systems disclosed herein may be used in connection with systems for treating cardiac arrest that are disclosed in U.S. Pat. No. 6,149,670, which is hereby incorporated by reference as if fully set forth herein. The catheters disclosed herein may also be used in connection with heating/cooling systems that are disclosed in U.S. Pat. Nos. 6,019,783 and 6,146,411 which are hereby incorporated by reference as if fully set forth herein. As set forth in FIG. 6a, to cool a patient as quickly as possible, the system's heat exchange capacity is set to its coldest temperature setting, for example a system bath temperature of about 0° C. A desired patient temperature target can be set by the operator. Once, the desired patient temperature target is met, the heat exchange capacity setting can be adjusted to maintain the patient temperature at the desired patient temperature target. In another embodiment (see FIG. 6b), to warm a patient to normothermia as quickly as possible, the system's heat exchange capacity should be set to its hottest temperature setting, for example a system bath temperature of about 49° C. A desired patient temperature target can be set by the operator. Once, the desired patient temperature target is met, the heat exchange capacity setting can be adjusted to maintain the patient temperature at the desired patient temperature target. Predearably, the desired patient temperature target is normothermia.

While the present invention has been described in terms of the preferred embodiments, other variations which are within the scope of the invention as defined in the claims will be apparent to those skilled in the art.

What is claimed is:

1. An intra-vascular catheter adapted to exchange heat with a body fluid flowing through a body conduit of a patient, comprising:

an elongate body including an inflow lumen and an outflow lumen each extending therethrough, at least one inflow duct and at least one inflation duct each in fluid communication with the inflow lumen, and at least one outflow duct in fluid communication with the outflow lumen;

at least one heat exchange element in fluid communication with the inflow lumen through at least one of the at least one inflow duct and in fluid communication with the outflow lumen through at least one of the at least one outflow ducts; and at least one inflation element disposed at least partially within the heat exchange element and in fluid communication with the inflow lumen through at least one of the at least one inflation duct.

2. The catheter of claim 1:

the at least one inflow duct including a first inflow duct and a second inflow duct; the at least one outflow duct including a first outflow duct and a second outflow duct; and the at least one inflation duct including a first inflation duct and a second inflation duct;

the at least one heat exchange element including a first heat exchange element in fluid communication with the first inflow duct and the first outflow duct, and a second heat exchange element in fluid communication with the second inflow duct and the second outflow duct;

the at least one inflation element including a first inflation element in fluid communication with the first inflation duct and a second inflation element in fluid communication with the second inflation duct.

3. The catheter of claim 1, at least one of the at least one inflation element being configured to promote mixing of the heat exchange fluid as the heat exchange fluid flows outside the inflation element.

4. The catheter of claim 3, the at least one of the at least one inflation element including a balloon having a substantially spiral configuration, and at least one of the at least one heat exchange element including a balloon having a substantially straight configuration.

5. The catheter of claim 1, at least one of the at least one inflation element having a maximum diameter that is approximately 50 percent to approximately 90 percent of a diameter of the heat exchange element.

6. An intra-vascular catheter adapted to exchange heat with a body fluid flowing through a body conduit of a patient, comprising:

an elongate body including inflow means for transporting a heat exchange fluid and outflow means for transporting the heat exchange fluid, each extending through the elongate body;

heat exchange means for exchanging heat between the heat exchange fluid and the body fluid in the patient's body conduit, the heat exchange means being in fluid communication with the inflow means and with the outflow means; and inflation element means for promoting mixing of the heat exchange fluid as the heat exchange fluid flows through the heat exchange means, the inflation element means being in fluid communication with the inflow means.

7. An intra-vascular catheter adapted to exchange heat with a body fluid flowing through a body conduit of a patient, comprising:

an elongate body including an inflow lumen, an outflow lumen and an inflation lumen each extending through the elongate body; at least one inflow duct in fluid communication with the inflow lumen; at least one outflow duct in fluid communication with the outflow lumen; and at least one inflation duct in fluid communication with the inflation lumen;

at least one heat exchange element in fluid communication with the inflow lumen through at least one of the at least one inflow duct and in fluid communication with the outflow lumen through at least one of the at least one outflow duct; and at least one inflation element disposed at least partially within the heat exchange element and in fluid communication with the inflation lumen through at least one of the at least one inflation duct.

8. The catheter of claim 7:

the at least one inflow duct including a first inflow duct and a second inflow duct, the at least one outflow duct including a first outflow duct and a second outflow duct; and the at least one inflation duct including a first inflation duct and a second inflation duct;

the at least one heat exchange element including a first heat exchange element in fluid communication with the first inflow duct and the first outflow duct, and a second heat exchange element in fluid communication with the second inflow duct and the second outflow duct;

the at least one inflation element including a first inflation element in fluid communication with the first inflation duct and a second inflation element in fluid communication with the second inflation duct.

9. The catheter of claim 7, at least one of the at least one inflation element being configured to promote mixing of the heat exchange fluid as the heat exchange fluid flows outside the inflation element.

10. The catheter of claim 9, the at least one of the at least one inflation element including a balloon having a substantially spiral configuration, and at least one of the at least one heat exchange element including a balloon having a substantially straight configuration.

11. The catheter of claim 9, the at least one of the at least one inflation element including a balloon having a substantially straight configuration, and at least one of the at least one heat exchange element including a balloon having a substantially spiral configuration.

12. An intra-vascular catheter adapted to exchange heat with a body fluid flowing through a body conduit of a patient, comprising:

an elongate body including inflow means for transporting a heat exchange fluid, outflow means for transporting the heat exchange fluid, and inflation means for transporting an inflation fluid, each extending through the elongate body;

heat exchange means for exchanging heat between the heat exchange fluid and the body fluid in the patient's body conduit, the heat exchange means being in fluid communication with the inflow means and with the outflow means; and inflation element means for promoting mixing of the heat exchange fluid as the heat exchange fluid flows through the heat exchange means, the inflation element means being in fluid communication with the inflation means.

13. An intra-vascular catheter adapted to exchange heat with a body fluid flowing through a body conduit of a patient, comprising:

an elongate body having an inflow lumen and an outflow lumen each extending therethrough, the inflow lumen and outflow lumen for conveying a heat exchange fluid through the elongate body;

at least one heat exchange element through which the heat exchange fluid may flow, the at least one heat exchange element being in fluid communication with the inflow lumen and the outflow lumen and covering a portion of the elongate body;

wherein at least part of the portion of the elongate body covered by the at least one heat exchange element has a configuration that promotes mixing of heat exchange fluid flowing through the heat exchange element.

14. The method for controlling a temperature of a patient and accessing a body fluid flowing through a body conduit of the patient, comprising the acts of:

providing an intra-vascular catheter including an elongate body, at least one heat exchange element disposed on the elongate body, and at least one inflation element disposed within at least one of the at least one heat exchange element;

inserting the catheter into a body conduit of a patient;

inflating at least one of the at least one inflation element;

circulating a heat exchange fluid through at least one of the at least one heat exchange element to effect heat transfer with the body fluid flowing through the body conduit.

15. The method of claim 14, the inflating step including the step of conveying an inflation fluid to the at least one of the at least one inflation element, a flow of the inflation fluid being controlled independently of a flow of the heat exchange fluid.

16. The method of claim 14, the at least one of the at least one inflation element being inflated with the heat exchange fluid.

* * * * *